US006995012B1

(12) United States Patent
Silverman et al.

(10) Patent No.: US 6,995,012 B1
(45) Date of Patent: Feb. 7, 2006

(54) **CLONING AND EXPRESSION OF RECOMBINANT ADHESIVE PROTEIN MEFP-2 OF THE BLUE MUSSEL, *MYTILUS EDULIS***

(75) Inventors: Heather G. Silverman, Idaho Falls, ID (US); Francisco F. Roberto, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 34 days.

(21) Appl. No.: 10/915,160

(22) Filed: Aug. 9, 2004

(51) Int. Cl.
*C12N 15/00* (2006.01)

(52) U.S. Cl. ............... 435/320.1; 435/69.1; 435/252.3; 536/23.5

(58) Field of Classification Search ............... 435/69.1, 435/252.3
See application file for complete search history.

(56) References Cited

U.S. PATENT DOCUMENTS 5,049,504 A * 9/1991 Maugh et al. ......... 435/252.33
5,202,236 A 4/1993 Maugh et al.
6,465,237 B1 10/2002 Tomlinson

OTHER PUBLICATIONS

Altschul, et al., Nucleic Acids Res. 25: 3389-3402 (1997).
Burzio, V.A., et al., Mussel Adhesive Enhances the Immobilization of Human Chorionic Gonadotrophin to a Solid Support, *Analytical Biochemistry*, 241 (2): 190-194 (1996).
Crisp, D.J., et al., Adhesion and Substrate Choice in Mussels and Barnacles, *Journal of Colloid and Interface Science,* 104(1): 40-50 (1985).
Inoue, K., et al., The Adhesive Protein cDNA of *Mytilus galloprovincialis* Encodes Decapeptide Repeats but No Hexapeptide Motif. *Biol. Bull.* 186: 349-355 (Jun. 1994).
Inoue, K., et al., Mussel Adhesive Plaque Protein Gene is a Novel Member of Epidermal Growth Factor-like Gene Family, *Journal of Biological Chemistry,* 270 (12): 6698-6701 (1995).
Karlin and Altschul, Proc. Nat'l. Acad. Sci. USA 87: 2264-2268 (1960).
Karlin and Altschul, Proc. Nat'l. Acad. Sci. USA 90: 5873-5877 (1993).
Miki, D., et al., Expression Sites of Two Byssal Protein Genes of *Mytilus galloprovincialis, Biol. Bull.* 190: 213-217 (Apr. 1996).
Papov, V.V., et al., Hydroxyarginine-Containing Polyphenolic Proteins in the Adhesive Plaques of the Marine Mussel, *Mytilus edulis, Journal of Biological Chemistry,* 270 (34): 20183-20192 (1995).
Qin, X.X., et al., Exotic Collagen Gradients in the Byssus of the Mussel, *Mytilus edulis, Journal of Experimental Biology,* 198(3): 633-644 (1995).
Qin, X.X., et al., A Potential Mediator of Collagenous Block Copolymer Gradients in Mussel Byssal Threads, *Proceedings of the National Academy of Sciences of the United States of America,* 95(18): 10517-10522 (1998).
Rzepecki, L.M., et al., Characterization of Cysteine-rich Polyphenolic Protein Family from the Blue Mussel, *Mytilus edulis-L,* Biological Bulletin, 183 (1): 123-137 (1992).
Saby, C., et al., *Mytilus edulis* Adhesive Protein (MAP) as an Enzyme Immobilization Matrix in the Fabrication of Enzyme-Based Electrodes, *Electroanalysis,* 10 (17): 1193-1199 (1998).
Sever, M.J., et al., Metal-mediated cross-linking in the generation of a marin-mussel adhesive, *Angewandte Chemie* 43(4), 448-450 (no date).
Vreeland, V., et al., Polyphenols and Oxidases in Substratum Adhesion by Marine Algae and Mussels, *Journal of Phycology,* 34 (1): 1-8 (1998).
Waite, J.H., Chem. Ind. p. 607 (1991).
Waite, J.H., Evidence for a Repeating 3,4-Dihydroxyphenylalanine-Containing and Hydroxyproline-Containing Decapeptide in the Adhesive Protein of the Mussel, *Mytilus edulis, Journal of Biological Chemistry,* 258(5): 2911-2915 (1983).
Waite, J.H., et al., Polyphenolic Substance of *Mytilus edulis* Novel Adhesive Containing L-Dopa and Hydroxyproline, *Science,* 212 (4498): 1038-1040 (1981).
Waite, J.H., et al., Polyphosphoprotein from the Adhesive Pads of Mytilus edulis, *Biochemistry*, 40 (9): 2887-2893 (2001).
Yu, M., et al., Role of L-3,4-Dihydroxyphenylalanine in Mussel Adhesive Proteins, *Journal of the American Chemical Society,* 121: 5825-5826 (1999).

* cited by examiner

*Primary Examiner*—Robert A. Wax
*Assistant Examiner*—Agnes Rooke
(74) *Attorney, Agent, or Firm*—Trask Britt, P.C.

(57) ABSTRACT

The present invention includes a *Mytilus edulis* cDNA having a nucleotide sequence that encodes for the *Mytilus edulis* foot protein-2 (Mefp-2), an example of a mollusk foot protein. Mefp-2 is an integral component of the blue mussels' adhesive protein complex, which allows the mussel to attach to objects underwater. The isolation, purification and sequencing of the Mefp-2 gene will allow researchers to produce Mefp-2 protein using genetic engineering techniques. The discovery of Mefp-2 gene sequences will also allow scientists to better understand how the blue mussel creates its waterproof adhesive protein complex.

24 Claims, 1 Drawing Sheet

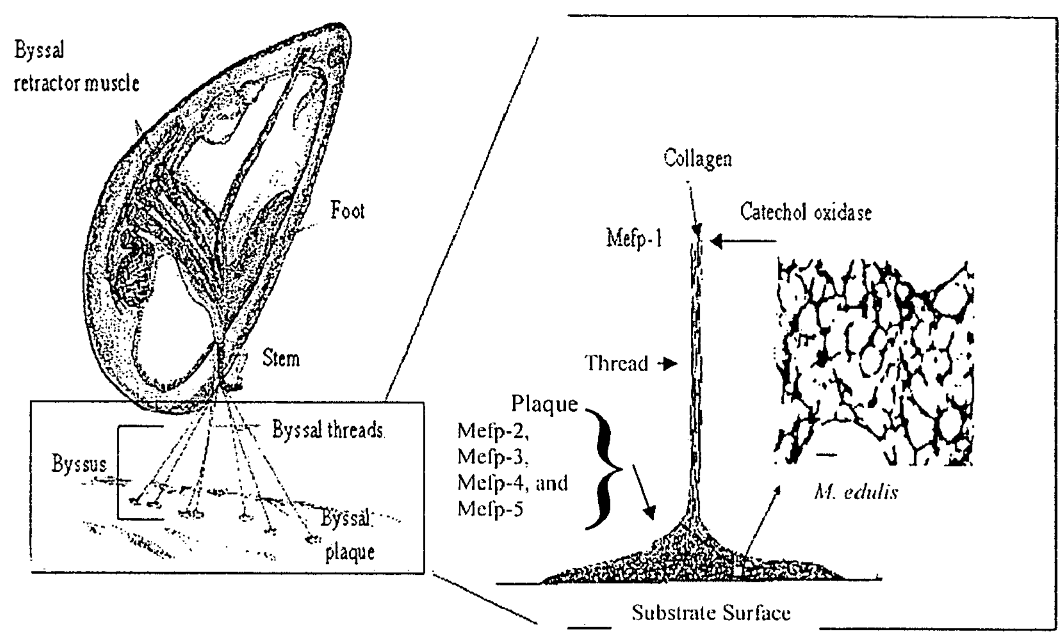
Byssal
retractor muscle
Foot
Stem
Byssal threads
Byssus
Byssal
plaque
Collagen
Catechol oxidase
Mefp-1
Thread
Plaque
Mefp-2,
Mefp-3,
Mefp-4, and
Mefp-5
M. edulis
Substrate Surface

CLONING AND EXPRESSION OF RECOMBINANT ADHESIVE PROTEIN MEFP-2 OF THE BLUE MUSSEL, *MYTILUS EDULIS*

U.S. GOVERNMENT RIGHTS

The United States Government has certain rights in this invention pursuant to Contract No DE-AC07-99ID13727, and Contract No DE-AC07-05ID14517 between the United States Department of Energy and Battelle Energy Alliance, LLC.

CROSS REFERENCED APPLICATIONS

This patent application was filed by Applicants on the same day as another patent application filed by Applicants entitled "CLONING AND EXPRESSION OF RECOMBINANT ADHESIVE PROTEIN MEFP-1 OF THE BLUE MUSSEL, *MYTILUS EDULIS*", having Ser. No. 10/915,161, filed Aug. 9, 2004.

TECHNICAL FIELD

The invention relates to isolated or purified nucleic acid molecules encoding an adhesive protein, for example, Mefp-2 of the blue mussel, *Mytilus edulis*. Adhesives that can be derived from the present invention can be used in a variety of fields including but not limited to: military applications, construction products, plastics, electronics, automobile and aviation products as well as several biomedical fields.

SEQUENCE LISTINGS

The electronic readable copy and paper copy of the sequence listing for this invention are identical.

BACKGROUND OF THE INVENTION

*Mytilus edulis*, also termed the common edible mussel or blue mussel, constitutes most of the world's commercial production of cultured mussels, along with the closely related species *Mytilus galloprovincialis*. Besides their use in food culturing, mussels (which is an example of a molusk) have also been used to monitor pollutants in coastal marine waters. The most extensive research about the adhesive properties of mussels has been with *M. edulis*.

Marine mussels, like the edible blue mussel, *M. edulis*, attach to a variety of surfaces in an aqueous environment using a natural adhesive that is incredibly strong and durable. There are no conventional glues that can be applied in an aqueous environment and are impervious to water and turbulent forces. Prior research has shown that one of the proteins in the adhesive, *Mytilus edulis* foot protein 1 (Mefp-1), bonds to glass, plastic, wood, concrete and Teflon. Nine other adhesive-related proteins from *M. edulis* have been identified to date. A tenth is implicated, but has not been identified. The precise mechanism for assembly of the ten proteins is not understood (Mefp-1, -2, -3, -4, -5; Collagens: Precollagen-D, —P (variant P22 and P33), Precollagen-NG, Proximal Matrix Thread Protein (1 and 1a); catechol oxidase). There also may be additional proteins involved in the formation of the adhesive.

Individual protein components have been previously identified from byssal structures through protein isolation and amino acid analysis, revealing repetitive amino acid motifs and modified amino acids with unique characteristics not found in other biological systems. Proposed mechanisms for the strength and waterproof properties of the adhesive formed, relate to these recurring amino acid motifs and hydroxylated amino acids found in many of the protein components. Commercial recombinant protein products consisting of either the partial amino acid sequence of Mefp-1 or repeats of the unique decapeptide motif have been marketed in the past. However, no commercial product incorporates any of the other proteins known to be involved in underwater adhesion by the *M. edulis* mussel. Furthermore, these products are a result of protein isolation techniques and NOT recombinant DNA techniques.

Initial strategies for identifying the adhesive proteins of the byssus of *M. edulis* involved purification of the proteins directly from the byssi of thousands of animals. About 10,000 mussels are needed to produce 1 gram of adhesive. Thus, subsequent purification and microscopic analysis require(d) the sacrifice of many mussels. This is neither environmentally friendly nor economically practical. When the original mussel adhesive protein, MAP, was identified, only the amino acid motif common to this protein, also referred to as Mefp-1, (a decapeptide repeat occurring ~80 times) was used in an alternate host production scheme. This MAP recombinant protein did/does have substantial adhesive properties; however, the (complete) gene sequence for Mefp-1 and the other proteins involved in byssus formation are necessary for mimicking the bioadhesive. In addition to a full length Mefp-1, isolating, purifying and sequencing the DNA sequence of *M. edulis* ' foot protein-2 (Mefp-2) are critically important and are objectives of the present invention.

The mussel byssus is an extracorporeal structure that consists of a stem, thread, and a plaque (also referred to as a pad or disc) (See FIG. 1) This exogenous attachment device was first described in Brown C H, Some Structural Proteins of *Mytilus edulis, Quarterly Journal of Microscopical Science*, 93(4): 487 (1952). High concentrations of polyphenolic proteins (e.g. L-DOPA), the presence of collagen, and the presence of a catechol oxidase were among the first observations of byssal attachments. Environmental factors such as salinity, temperature, pH, season, and substratum choice, as well as biological factors such as age and metabolic state of the animal effect the efficiency and strength of bonding/attachment. See Crisp D J, Walker G, Young G A, Yule A B, Adhesion and Substrate Choice in Mussels and Barnacles, *Journal of Colloid and Interface Science,* 104 (1): 40–50 (1985).

The stem is rooted in the byssal retractor muscles at the base of the foot organ. See Crisp D J, Walker G, Young G A, Yule A B, Adhesion and Substrate Choice in Mussels and Barnacles, *Journal of Colloid and Interface Science,* 104 (1): 40–50 (1985). The byssal threads, flexible structures of variable dimensions (e.g. ~0.1 mm diameter, 2–4 cm length) and strength, originate from the stem. A byssal thread consists of a flexible, collagenous inner core surrounded by a hard, browned polyphenolic protein. Numerous researchers photographed the collagen core in the 1930's (See Brown C H, Some Structural Proteins of *Mytilus edulis, Quarterly Journal of Microscopical Science,* 93(4): 487 (1952))—well before three unique, collagenous proteins were identified and characterized by J. H. Waite and colleagues. The outer polyphenolic protein, believed to undergo a curing or quinone tanning-type reaction with a specialized catechol/polyphenol oxidase enzyme, is traditionally designated as *Mytilus edulis* foot protein 1, Mefp-1, or MAP. (Designation of the byssal thread polyphenolic adhesive protein, as well as subsequent adhesive proteins identified in *M. edulis*, is preceded by the genus and species: e.g. *Mytilus edulis* foot protein 1=Mefp-1).

The breaking energy of byssal threads is reported to be $12.50\times10^6$ $Jm^{-3}$, vs tendon ($2\times10^6$ $Jm^{-3}$ to $5\times10^6$ $Jm^{-3}$) and silk ($50\times10^6$ $Jm^{-3}$ to $180\times10^6$ $Jm^{-3}$; See Denny M W, *Biology and the Mechanics of the Wave Swept Environment*, Princeton: Princeton University Press (1988); Qin X X, Waite J H, Exotic Collagen Gradients in the Byssus of the Mussel, *Mytilus edulis, Journal of Experimental Biology*, 198 (3): 633–644 (1995). Bond strengths range from 0.1 to $10\times10^6$ $Nm^{-2}$ depending on the substratum. (See Waite J H, Reverse Engineering of Bioadhesion in Marine Mussels, *Bioartificial Organs II: Technology, Medicine, and Materials Annals of the New York Academy of Sciences,* 875: 301–309 (1999)). Byssal thread strength at the distal portion of threads is as strong as vertebrate tendon, but 3–5× more extensible (see, Qin X X, Waite J H, A Potential Mediator of Collagenous Block Copolymer Gradients in Mussel Byssal Threads, *Proceedings of the National Academy of Sciences of the United States of America,* 95 (18):10517–10522 (1998)). Byssal thread strength at the proximal portion of threads is weaker, but 15–20× more extensible. Strain energy density of threads approaches that of silk at approximately 6× tougher than tendon. Byssal threads can recover initial length and stiffness given sufficient relaxation time (See Bell E C, Gosline J M, Mechanical Design of Mussel Byssus: Material Yield Enhances Attachment Strength, *Journal of Experimental Biology,* 199 (4): 1005–1017 (1996). The byssal structure culminates in a polyphasic plaque of varying size, dependent upon both the size of the animal and the age of the byssus (See Crisp D J, Walker G, Young G A, Yule A B, Adhesion and Substrate Choice in Mussels and Barnacles, *Journal of Colloid and Interface Science,* 104 (1): 40–50 (1985). Plaques are commonly only ~0.15 mm in diameter where they meet the thread, and ~2–3 mm diameter at the substrate interface. Plaque formation occurs from the deposition of proteins that originate from the foot organ. To date, four specialized adhesive proteins have been identified in byssal plaques from *M. edulis*: Mefp-2, Mefp-3, Mefp-4 and Mefp-5.

In spite of the extensive research in this area, and relative success in patenting and commercializing aspects of these adhesive proteins, a complete understanding of how the byssus is assembled from its component proteins, and the role each protein plays in successful assembly and attachment has not been achieved. A major hurdle has been, and remains, large-scale production of protein in quantities to allow extensive study outside of the byssus. This invention describes nucleotide sequences from cDNAs for Mefp-2 for the first time.

SUMMARY OF THE INVENTION

One aspect of the invention is an isolated and purified nucleic acid comprising the nucleotide sequence in (SEQ ID. NO: 1; a c-DNA sequence) which encodes a biologically active Mefp-2 peptide fragment.

Another aspect of the invention is an isolated and purified nucleic acid comprising the nucleotide sequence in (SEQ ID. NO: 3; a c-DNA sequence) which encodes a biologically active Mefp-2 peptide fragment.

Another aspect of the invention is an isolated and purified nucleic acid comprising the nucleotide sequence in (SEQ ID. NO: 5; a c-DNA sequence) which encodes a biologically active Mefp-2 peptide fragment.

The invention also relates to methods of using the isolated and purified DNA sequences to express the polypeptides which they encode.

Yet another aspect of the invention is a method of producing Mefp-2 protein which comprises incorporating the nucleic acids having the sequences provided by this invention into an expression vector, transforming a host cell with the vector and culturing the transformed host cell under conditions which result in expression of the gene.

Another aspect of the invention is a nucleic acid sequence that is capable of hybridizing under stringent conditions to a nucleotide sequence found in (SEQ ID NO: 1), (SEQ ID NO: 3) or (SEQ ID NO: 5), or their complements.

Another aspect of the invention is a nucleic acid molecule that includes the nucleotide sequence set forth in (SEQ ID NO: 1), (SEQ ID NO: 3) or (SEQ ID NO: 5), or degenerate variants thereof.

Another aspect of the invention is an RNA molecule that includes the nucleotide sequence set forth in (SEQ ID NO: 1), (SEQ ID NO: 3) or (SEQ ID NO: 5), or degenerate variants thereof, wherein Uracil (U) is substituted for Thymine (T).

Also included in the invention are nucleotides carrying modifications such as substitutions, small deletions, insertions or inversions which still encode proteins having substantially the same activity as the protein of (SEQ ID NO: 2), (SEQ ID NO: 4) or (SEQ ID NO: 6). Included are nucleic acid molecules having a sequence which is at least 90% identical to the nucleotide sequence shown in (SEQ ID NO: 1), (SEQ ID NO: 3) or (SEQ ID NO: 5) respectively.

Another aspect of this invention is genetically engineered polypeptides created using the isolated and purified nucleotide sequences of this invention.

Yet another aspect of this invention is utilizing the genetically engineered polypeptides created using the isolated and purified nucleotide sequences of this invention.

BRIEF DESCRIPTION OF THE DRAWINGS

FIG. 1 is a schematic illustration of the byssal structures of *M. edulis* adapted from Waite J. H., Chem. Ind. p. 607 (1991) and Waite J. H, J. Comp. Physiol (B), p. 451 (1986).

DETAILED DESCRIPTION OF THE PREFERRED EMBODIMENTS

In practicing the present invention several conventional techniques in microbiology and molecular biology (recombinant DNA) are used. Such techniques are well known and are explained in, for example, Sambrook, 1999, Molecular Cloning: A Laboratory Manual, Second Edition, Cold Spring Harbor Laboratory Press, Cold Spring Harbor, N.Y.; DNA Cloning: A practical Approach, 1985 (D. N. Glover ed); Current Protocols in Molecular Biology, John Wiley & Sons, Inc. (1994) and all more recent editions of these publications.

Definitions

Before proceeding further with a description of the specific embodiments of the present invention, a number of terms will be defined.

As used herein, a compound or molecule is an organic or inorganic assembly of atoms of any size, and can include macromolecules, peptides, polypeptides, whole proteins, and polynucleotides.

As used herein, a polynucleotide is a nucleic acid of more than one nucleotide. A polynucleotide can be made up of multiple poly-nucleotide units that are referred to be a description of the unit. For example, a polynucleotide can comprise within its bounds a polynucleotide(s) having a coding sequence(s), a polynucleotide(s) that is a regulatory region(s) and/or other polynucleotide units commonly used in the art.

The isolated nucleic acid molecule of the present invention can include a deoxyribonucleic acid molecule (DNA), such as genomic DNA and complementary cDNA which can be single (coding or noncoding strand) or double stranded, as well as synthetic DNA, such as synthesized single stranded polynucleotide. The isolated nucleic acid molecule of the present invention can also include a ribonucleic acid molecule (RNA).

The determination of percent identity or homology between two sequences is accomplished using the algorithm of Karlin and Altschul (1990) Proc. Nat'l Acad. Sci. USA 87: 2264–2268, modified as in Karlin and Altschul (1993) Proc. Nat'l Acad. Sci. USA 90:5873–5877. Such an algorithm is incorporated into the NBLAST and XBLAST programs of Altschul et al. (1990) J. Mol. Biol. 215:403–410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) Nucleic Acids Res. 25: 3389–3402. When utilizing BLAST and Gapped BLAST programs, the default parameters of the respective programs (e.g., XBLAST and NBLAST) are used. See the website for the national center for biological information.

As used herein, the terms hybridization (hybridizing) and specificity (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency, which include: temperature, solvent ratios, salt concentrations, and the like.

In particular, selective hybridization pertains to conditions in which the degree of hybridization of a polynucleotide of the invention to its target would require complete or nearly complete complementarity. The complementarity must be sufficiently high as to assure that the polynucleotide of the invention will bind specifically to the target relative to binding other nucleic acids present in the hybridization medium. With selective hybridization, complementarity will be 90–100%, preferably 95–100%, more preferably 100%.

The term stringent conditions is known in the art from standard protocols (e.g. Current Protocols in Molecular Biology, editors F. Ausubel et al., John Wiley and Sons, Inc. 1994) and is when hydridization to a filter-bound DNA in 0.5M $NaHPO_4$ (pH7.2), 7% sodium dodecyl sulfate (SDS), 1 mM EDTA at +65° C., and washing in 0.1×SSC/0.1% SDS at +68° C. is performed.

Degenerate variant is the redundancy or degeneracy of the genetic code as is well known in the art. Thus the nucleic acid sequences shown in the sequence listing provided only examples within a larger group of nucleic acids sequences that encode for the polypeptide desired.

Isolated nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays.

Because the genetic code is degenerate, more than one codon may be used to encode a particular amino acid, and therefore, the amino acid sequence can be encoded by any set of similar DNA oligonucleotides. With respect to nucleotides, therefore, the term derivative(s) is also intended to encompass those DNA sequences that contain alternative codons which code for the eventual translation of the identical amino acid.

Mussel adhesive proteins are scleroproteins—proteins contributing mechanical strength to supporting structures in animals. Familiar scleroproteins include collagen, silk, elastin, fibroin, keratin, fibrin and resilin. Quinone tanning requires a catecholic precursor (such as catechol oxidase) and the presence of tanned scleroproteins. See, Waite J H, The Phylogeny and Chemical Diversity of Quinone-tanned Glues and Varnishes, *Comp Biochem Physiol B.,* 97(1): 19–29 (1990). Individual adhesive proteins from mussels are derived from the foot organ of the animals. The proteins are stockpiled in the foot, and then secreted or released into the environment to form strong attachments underwater. The proteins involved in adhesion of mussels contain peptidyl-3–4,-dihydroxy-phenylalanine (DOPA), a constituent not found in barnacle cement proteins. The reactive, oxidized form of DOPA, quinone, is thought to provide the moisture-resistance characteristic of mussel underwater adhesion. See, Yu M, Hwang, J, Deming, TJ, Role of L-3,4-Dihydroxyphenylalanine in Mussel Adhesive Proteins, *Journal of the American Chemical Society,* 121: 5825–5826 (1999). DOPA can complex with metal ions and oxides and semi-metals such as silicone, thus explaining the ability to adhere to rocks and glass. Other constituents of mussel adhesive proteins include lysine and glycine. Lysine may contribute to adhesion via ionic bonding to negatively charged surfaces like collagen and acidic polysaccharides. Proposed mechanisms for the strength and waterproof properties of the adhesive formed relate to recurring amino acid motifs (decapeptide repeats of 75–80 times in Mefp-1) and the hydroxylated amino acids found in the adhesive proteins. Polyphenolic proteins are non-toxic, biodegradable and have a low immunogenicity.

Mefp-1 is a polyphenolic protein with primarily structural properties. It is oxidized and cross-linked through the action of a catechol oxidase to form a hardened sheath (the byssal thread) that extends between the foot organ of the animal and the surface of attachment. The inner core of this structure is comprised of four collagens (with variants) with distinctive domains not found in other biological systems. This combination of proteins functions much like a natural epoxy adhesive. The cystine-rich Mefp-2 forms the foam-like plaque component of the byssus. Mefp-4 and Mefp-5 are additional proteins located in the plaque. A hydroxyarginine-containing protein, Mefp-3, is believed to serve as a primer-like protein for this byssal plaque.

Byssal Plaque Polyphenolic Protein: Mefp-2

Mefp-2 is found exclusively in byssal plaques, constituting from 25–40% of the total plaque proteins. Unlike Mefp-1, Mefp-2 is a smaller adhesive protein (molecular mass 42–47 kDa) with only 2–3 mol % DOPA and no hydroxylation of proline to trans-2,3-cis-3,4-dihydroxyproline or trans-4-hydroxy-L-proline. The DOPA residues occur primarily in the N- and C-terminal regions of the protein. Mefp-2 contains considerable secondary structure and is relatively resistant to a variety of proteases (compared to Mefp-1). The high cysteine content (6–7 mol %) coupled with tandemly repetitive motifs similar to epidermal growth factor, represents an adhesive protein with a stabilization role in the byssus (See Inoue K, Takeuchi Y, Miki D, Odo S, Mussel Adhesive Plaque Protein Gene is a Novel Member of Epidermal Growth Factor-like Gene Family, Journal of Biological Chemistry, 270 (12): 6698–6701 (1995).

An Mefp-2 multi-gene family may exist, based on evidence that at least three different repetitive motifs have been identified in the primary protein sequence (See Rzepecki L M, Hansen K M, Waite J H, Characterization of Cysteine-rich Polyphenolic Protein Family from the Blue Mussel, *Mytilus edulis*-L, Biological Bulletin, 183 (1): 123–137 (1992). A published full-length gene sequence for Mefp-2 has not been available until now.

Other Byssal Proteins: Mefp-1, Mefp-3, Mefp-4 and Mefp-5

Mefp-1

Mefp-1 was the first polyphenolic protein to be identified in the mussel byssus (See Waite J H, Tanzer M L, Polyphenolic Substance of *Mytilus edulis* Novel Adhesive Containing L-Dopa and Hydroxyproline, *Science,* 212 (4498): 1038–1040 (1981). The primary location of Mefp-1 is in the byssal threads, cross-linked via a polyphenol oxidase to form a schlerotonized sheath around the flexible, collagen inner-core. Byssal plaques contain approximately 5% of Mefp-1 as well. Mefp-1 adhesive properties are comparable to synthetic cyanoacrylate and epoxy resins.

Mefp-1 is a large, basic protein with very little secondary structure and a molecular mass of 130 kDa. Decapeptide and hexapeptide repeats containing numerous post-translational modifications (~60–70% of the amino acid residues are hydroxylated) provided the first indication of an adhesive-related protein unlike any others identified in nature. The hexapeptide repeat is AKPTYK (SEQ ID NO: 22). The major decapeptide consensus repeat, consisting of AKPSY PPTYK (SEQ ID NO: 23) (where Y represents 3,4-dihydroxyphenyl-alanine (DOPA), "P" represents trans-2,3-cis-3,4-dihydroxyproline, and P represents trans-4-hydroxy-L-proline) occurs approximately eighty times in Mefp-1. DOPA residues constitute 10–15% of the protein (See Waite J H, Evidence for a Repeating 3,4-Dihydroxyphenylalanine-Containing and Hydroxyproline-Containing Decapeptide in the Adhesive Protein of the Mussel, *Mytilus edulis, Journal of Biological Chemistry,* 258 (5): 2911–2915 (1983). The open conformation of the protein is believed to allow functional groups full accessibility for interactions with other proteins and a variety of surfaces, including glass, Teflon, and metals.

Mefp-1 has been previously commercialized as a source for mussel adhesive protein. Companies supplying Mefp-1 have obtained the pure protein from the byssal structures using protein extraction techniques (e.g., Sigma-Aldrich; BD Biosciences Clontech, formerly marketed by BioPolymers Corp of Farmington, Conn., under the trademark CELL-TAK®) and recombinant protein techniques using synthetic gene constructs. However, currently there are no commercial sources for Mefp-1, due to the high cost of extraction methods and inconsistencies in quality of protein from recombinant protein techniques. All of the laboratory-prepared products were not as strong as the natural protein.

Mefp-1 requires oxidization by catechol oxidase or tyrosinase enzymes (or periodontate) in order to render the tyrosine residues converted to reactive DOPA residues required for strong adhesion. The enzyme oxidation may serve as an oxidative agent and as a copolymer. Molecular oxygen can also be used to oxidize DOPA to a quinone. Possible cross-linking agents are oxygen, polyvalent metal ions, $Fe^{3+}$ and $Al^{3+}$, aldehydes and many types of bi/poly-functional cross-linkers. The addition of other macromolecules to the Mefp-1 protein—such as collagen, casein or keratin—has been recommended by companies in order to increase the adhesive properties of the individual protein.

Mefp-1 in the form of CELL-TAK (BioPolymers Corp of Farmington, Conn.) has been tested as a surgical adhesive between a number of different cells or tissues from a range of species. For example, studies testing the efficiency of CELL-TAK (BioPolymers Corp of Farmington, Conn.) compared to other adhesives have included porcine cartilage, bone and skin (see, Chivers R A, Wolowacz R G, The Strength of Adhesive-Bonded Tissue Joints, International Journal of Adhesion and Adhesives, 17 (2): 127–132 (1997)), rat tissue (see, Schmidt S P, Resser J R, Sims R L, Mullins D L, Smith D J, The Combined Effects of Glycyl-L-Histidyl-L-Lysine-Copper (II) and CELL-TAK® ((BioPolymers Corp of Farmington, Conn.) on the Healing of Linear Incision Wounds, Wounds A Compendium of Clinical Research and Practice, 6 (2):62–67 (1994)), rabbit corneas (see, Robin J B, Picciano P, Kusleika R S, Salazar J, Benedict C, Preliminary Evaluation of the Use of Mussel Adhesive Protein in Experimental Epikeratoplasty, Archives of Ophthalmology, 106 (7):973–977 (1988)), and chicken osteoblasts and cartilage cells (see, Fulkerson J P, Norton L A, Gronowicz G, Picciano P, Massicotte J M, Nissen C W, Attachment of Epiphyseal Cartilage Cells and 17/28 Rat Osterosarcoma Osteoblasts using Mussel Adhesive Protein, Journal of Orthopaedic Research, 8 (6): 793–798 (1990)). Studies have also included human breast cancer cells and mouse sperm cells. The best adhesion with CELL-TAK (BioPolymers Corp of Farmington, Conn.) has been shown to occur with cell cultures. Other testing of CELL-TAK for industrial applications has included it's use as an enzyme immobilization matrix in the fabrication of enzyme-based electrodes (See Saby C, Luong J H T, *Mytilus edulis* Adhesive Protein (MAP) as an Enzyme Immobilization Matrix in the Fabrication of Enzyme-Based Electrodes, Electroanalysis, 10 (17): 1193–1199 (1998)).

Purified polyphenolic protein was also shown to effectively immobilize human chorionic gonadotrophin to wells of a microtiter plate (See Burzio V A, Silva T, Pardo J, Burzio L O, Mussel Adhesive Enhances the Immobilization of Human Chorionic Gonadotrophin to a Solid Support, Analytical Biochemistry, 241 (2): 190–194 (1996). In addition, the immunoreactivity of the attached antigen used in the study was stable for several months. This example shows a possible tool for polyphenolic proteins in basic research and medical diagnostics.

Other *Mytilus* mussel species contain a protein analogous to Mefp-1, with differences in the decapeptide repeat frequency, residue composition, and non-repetitive regions. To date, analogous proteins to Mgfp-2 have not been reported other than the identification of the Mefp-2 variants described herein.

Mefp-3

Mefp-3 is the smallest byssal adhesive protein identified to date, with a molecular mass of –5–7 kDa. See Papov V V, Diamond T V, Biemann K, Waite J H, Hydroxyarginine-Containing Polyphenolic Proteins in the Adhesive Plaques of the Marine Mussel, *Mytilus edulis*, Journal of Biological Chemistry, 270 (34): 20183–20192 (1995); Inoue K, Takeuchi Y, Miki D, Odo S, Harayama S, Waite J H, Cloning, Sequencing and Sites of Expression of Genes for the Hydroxyarginine-Containing Adhesive-Plaque Protein of the Mussel, *Mytilus galloprovincialis*, European Journal of Biochemistry, 239 (1): 172–176 (1996); Warner S C, Waite J H, Expression of Multiple Forms of an Adhesive Plaque Protein in an Individual Mussel, *Mytilus edulis*, Marine Biology, 134 (4): 729–734 (1999). Mefp-3 contains no repeats, 20–25 mol % DOPA, and a prevalence of 4-hydroxyarginine and tryptophan residues. Warner S C, Waite J H, "Expression of Multiple Forms of an Adhesive Plaque Protein in an Individual Mussel, *Mytilus edulis*", Marine Biology, 134 (4): 729–734 (1999) identified twenty gene variants (~0.3 kB) of Mefp-3 in the foot organ; however, only four or five proteins have actually been detected in plaques deposited on glass or plastic. The presence of a gene family for Mefp-3 supports the primer-like function of the protein in adhering to substrata. One hypothesis has been that deposition of a specific Mefp-3 variant is dependent upon the surface used for attachment. However, protein expression specific to substrate attachment has not been demonstrated to date.

Mefp-4

Mefp-4 is another protein identified in byssal plaques, with a molecular mass of 79 kDa (See, Warner S C, Waite J H, "Expression of Multiple Forms of an Adhesive Plaque Protein in an Individual Mussel, *Mytilus edulis*", Marine Biology, 134 (4): 729–734 (1999); Vreeland V, Waite J H, Epstein L, "Polyphenols and Oxidases in Substratum Adhesion by Marine Algae and Mussels", Journal of Phycology, 34 (1): 1–8 (1998); Weaver, J K, "Isolation, Purification, and Partial Characterization of a Mussel Byssal Precursor Protein, *Mytilus edulis* foot protein 4", MS thesis, University of Delaware, Newark, (1998).

Mefp-4 contains elevated levels of glycine, arginine, and histidine, as well as 4 mol % DOPA. A unique tyrosine-rich octapeptide is present, with variations in residue substitutions giving rise to a family of proteins. This very large protein most likely serves a stabilization role in byssal plaques, as does Mefp-2. A gene sequence for Mefp-4 has not been identified, nor are any analogs/homologs from other mussel species available to date.

Mefp-5

Mefp-5 is the most recent identified adhesive-related byssal plaque protein. See, Waite J H, Qin X X, "Polyphosphoprotein from the Adhesive Pads of *Mytilus edulis*", Biochemistry, 40 (9): 2887–2893 (2001). Mefp-5 is a relatively small protein with a molecular mass of 9.5 kDa, a 27 mol % DOPA content, and the presence of phosphoserine. Phosphoserine is known to occur in acidic mineral-binding motifs of proteins that bind calcareous materials (e.g. osteopontin); therefore, its presence in byssal plaques may aid in adhesion of one animal to a neighboring mussel's shell. Mefp-5 was formerly associated with the Mefp-3 family of variants, and similarly, plays an interfacial role as a primer for substrate adhesion. See, also M J Sever, et al., Metal-mediated cross-linking in the generation of a marin-mussel adhesive. Angewandte Chemie 43(4), 448–450.

An underwater adhesive will be a valuable asset to the military and industries such as forest products (composite wood products), building/construction, plastics, electronics, automotive, aviation, and the biomedical fields (dentistry, surgery, orthopedics, ophthalmology). All can benefit from an environmentally safe, strong, inexpensive alternative to the conventional adhesives available today. There are no conventional glues that can be applied in an aqueous environment and are impervious to water and turbulent forces. The development of a biomimetic glue product (an adhesive that employs man-made materials to mimic the efficient attachment mechanisms of the natural mussel) will revolutionize the field of adhesive technology. Mussel adhesive proteins represent a tantalizing target in the field of biomimetics. The challenge of resisting the effects of water: (i) its ability through hydrogen bonding to interfere with initial bonding between the substrate and adhesive; (ii) the attack by water on the adhesive-substrate interface through wicking and crazing; (iii) swelling of adhesive (and failure of the bond junction) through water absorption; and (iv) dissolution or erosion of the adhesive, have been met by the mussel byssus and the protein constituents secreted during its synthesis. For more than 20 years, researchers have studied mussel adhesion to gain clues to design better glues for wet environments, such as in dentistry, as a surgical glue and in industry. Two commercial products for attachment of cells to plastic vessels in cell culture applications have been introduced (Cell-Tak/BioPolymers, Inc., AdheraCell/Genex Corp.), and several U.S. patents cover aspects of the repeating decapeptide motif, isolation of polyphenolic proteins from mussels and recombinant forms of Mefp-1.

Genetic Approaches

Reverse-genetics approaches to obtaining complete gene sequences, enzymatic screening of a cDNA library from the foot organ of *M. edulis*, and the use of DNA probes allow for detection of transcripts actively expressed and transcribed by the mussel. With the complete gene sequences, an alternate host system can be employed to produce the adhesive proteins of interest for future analyses from protein chemistry, novel microscopy, and adhesive science disciplines. The adhesives industry will require a large quantity of protein to perform adequate testing and analyses for future adhesive technologies.

In the first reverse-genetics strategy, an approach is taken to identify known genes for adhesive proteins of interest. For this method, PCR (polymerase chain reaction) primers are designed for the genes of interest based on available nucleotide and amino acid sequences from *M. edulis* and other mussel species. The primers are combined with total RNA isolated from the foot organ of *M. edulis* in an RT-PCR (reverse transcription followed by PCR) reaction to yield a product corresponding to the gene of interest. This cDNA (c="complementary") product is then inserted (cloned) into a plasmid vector (currently obtained from a vendor). The clone for the adhesive gene of interest is now packaged for analysis by DNA sequencing and for insertion (transformation) into a suitable host for recombinant protein expression. DNA sequencing of the clone is critical in 1) determining that the clone is full-length e.g. contains the start and stop signal for translation of the full gene to protein, and 2) identifying variants in any of the gene sequences.

In the second reverse-genetics approach, a cDNA library is constructed from RNA isolated from the foot organ of *M. edulis*. This library consists of individual clones in wells of a microtiter plate. High-throughput DNA sequencing of the microtiter plates containing the clones, followed by analysis using available bioinformatics software programs, will enable 1) a determination of all of the genes presently expressed in the foot of the mussel, and 2) a determination of known and possibly novel adhesive proteins expressed in the foot of the mussel. The treatment of mussels prior to excision of their foot organ for RNA isolation (e.g. exposure to various surfaces, water conditions) may play a role in the expression of genes in the foot organ.

An enzymatic assay is a third strategy to obtain the polyphenoloxidase (catechol oxidase) gene. In this assay, microtiter plates containing either 1) all clones from a foot organ cDNA library or 2) only clones identified by DNA sequencing to resemble a polyphenoloxidase enzyme, are subjected to addition of an appropriate substrate for colorimetric indication of active enzyme activity. It is important that the active form of the protein be determined for subsequent adhesive formulation determinations.

A fourth strategy to obtain genes for adhesive proteins involves the development of nucleotide probes based on known DNA sequences or protein sequence motifs in the respective genes. These probes are then tested against a cDNA foot library from *M. edulis*.

PREFERRED EMBODIMENTS

The present invention relates to the adhesive protein, Mepf-2 and the nucleotide sequences encoding such protein, found in the blue mussel, *Mytilus edulis*. Sequence ID NO: 1, SEQ ID NO: 3 and SEQ ID NO: 5 describe the DNA sequence encoding Mepf-2 (SEQ ID NOs: 1, 2, and 3 are representative of the coding sequence, since they were generated from c-DNAs). (Sequence ID NO: 2), (SEQ ID NO: 4) and (SEQ ID NO: 6) illustrate the corresponding amino acid sequences for the abovementioned nucleotide sequences.

Nucleotide Sequences

The scope of the present invention is not limited to the exact sequence of the nucleotide sequences set forth in (SEQ ID NO: 1), (SEQ ID NO: 3) and (SEQ ID NO: 5) or the use thereof. The invention contemplates certain modifications to the sequence, including deletions, insertions, and substitutions, that are well known to those skilled in the art. For example, the invention contemplates modifications to the sequence found in (SEQ ID NO:1), (SEQ ID NO: 3) and (SEQ ID NO: 5) with codons that encode amino acids that are chemically equivalent to the amino acids in the native protein. An amino acid substitution involving the substitution of amino acid with a chemically equivalent amino acid includes a conserved amino acid substitution.

Chemical equivalency can be determined by one or more the following characteristics: charge, size, hydrophobicity/hydrophilicity, cyclic/non-cyclic, aromatic/non-aromatic etc. For example, a codon encoding a neutral non-polar amino acid can be substituted with another codon that encodes a neutral non-polar amino acid, with a reasonable expectation of producing a biologically equivalent protein.

Amino acids can generally be classified into four groups. Acidic residues are hydrophilic and have a negative charge to loss of $H^+$ at physiological pH. Basic residues are also hydrophilic but have a positive charge to association with $H^+$ at physiological pH. Neutral nonpolar residues are hydrophobic and are not charged at physiological pH. Neutral polar residues are hydrophilic and are not charged at physiological pH. Amino acid residues can be further classified as cyclic or noncyclic and aromatic or nonaromatic, self-explanatory classifications with respect to side chain substituent groups of the residues, and as small or large. The residue is considered small if it contains a total of 4 carbon atoms or less, inclusive of the carboxyl carbon. Small residues are always non-aromatic.

Of naturally occurring amino acids, aspartic acid and glutamic acid are acidic; arginine and lysine are basic and noncylclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic is a special case due to its known effects on secondary conformation of peptide chains, and is not, therefore included in this defined group.

There are also common amino acids which are not encoded by the genetic code include by example and not limitation: sarcosine, beta-alanine, 2,3-diamino propionic and alpha-aminisobutryric acid which are neutral, nonpolar and small; t-butylalanine, t-butylglycine, methylisoleucine, norleucine and cyclohexylalanine which are neutral, nonpolar, large and nonaromatic; ornithine which is basic and non-cylclic; cysteic acid which is acidic; citrulline, acetyl lysine and methionine sulfoxide which are neutral, polar, large and nonaromatic; and phenylglycine, 2-naphtylalanine, B-2-thienylalanine and 1,2,3,4-tetrahydroisoquinoline-3-carboxylic acid which are neutral, nonpolar, large and aromatic. Other modifications are known in the art some of which are discussed in U.S. Pat. No. 6,465,237 issued to Tomlinson on Oct. 15, 2002.

Cloning and Sequencing of cDNA Encoding Mepf-2: SEQ ID NO: 1, 3, and 5

For SEQ ID NO: 5 (clone designation QTB10): Total RNA from the foot organ of *M. edulis* was supplied to the customer by Invitrogen Corporation (Carlsbad, Calif.). Invitrogen's cDNA library was constructed using the following strategy. First strand cDNA was synthesized using AMV Reverse Transcriptase with a Not T primer. The Not I primer is a 39 base pair primer which consists of 18 T residues and a Not I restriction site. The RNA-cDNA hybrid created by first strand synthesis was converted to double stranded cDNA by DNA Polymerase I in combination with RNase H and *E. coli* DNA ligase. After addition of BstX I adapters, the cDNA was digested with Not I and sized on an agarose gel. Size selected cDNA (>500 bp) was ligated into BstX I/Not I digested phagemid vector pYES2 and transformed into the *E. coli* strain TOP10F'. pYES2 is a yeast expression vector. Library amplification was performed by plating over 20 large plates and incubating overnight at 37° C. The cells were scraped from the plates, resuspended into SOC media/20% glycerol and aliquoted into 6 tubes with each vial containing approximately 2 mL. Vials were stored at 80° C. until use. Validation: number of primary recombinants=$4.35\times10^6$ ratio containing inserts=10/10, average insert size of the clones analyzed=1.22 kB. The original cDNA library from Invitrogen was designated as #1 (I). Subsequent replications and platings were designated as cDNA libraries #2 (II) and #3 (III).

TABLE 1

Primers for RT-PCR: Mefp-2 (SEQ ID NO: 1 and 3)

| Primer | F/R | Target | DNA Sequence: 5' to 3' | nt | Restriction Site | Amino Acids |
|---|---|---|---|---|---|---|
| 514 | F | Mefp-2 | gcggccgccacagaagcatcatgttgttttc (SEQ ID NO: 17) | 31 | Not I | . . . MLFS (SEQ ID NO: 20) |
| 515 | R | Mefp-2 | gagctcgtctaggttaacttaatactcgtc (SEQ ID NO: 18) | 30 | Sac I | . . . DEY* (SEQ ID NO: 21) |

For SEQ ID NO: 1 and 3: Specific primers were designed (as shown in Table 1) based upon GenBank Accession No. D43794, *Mytilus galloprovincialis* (SEQ ID NO: 19) mRNA for adhesive plaque matrix protein. Primer set 514(SEQ ID NO: 17)/515(SEQ ID NO: 18) produced clones #2 (SEQ ID NO: 1) and #7 (SEQ ID NO: 3) The *M. galloprovincialis* sequence was used because it was assumed an analogous protein is present in *M. edulis.*

The nucleotide sequence for Mepf-2 clone #2 (SEQ ID NO: 1) and clone # 7 (SEQ ID NO: 3) was amplified by RT-PCR using the designed primers with total RNA isolated from the foot organ of *M. edulis*. Following first strand cDNA synthesis, PCR was carried out as described for clone #2: 1 $\mu$L cDNA, 5 $\mu$L 10× Buffer for Accuzyme DNA Polymerase (for a 2 mM $MgCl_2$ final concentration; Bioline; Randolph, Mass.), 1 $\mu$L dNTPs (at 10 mM each), 2 $\mu$L primer set 514 (SEQ ID NO: 17)/515(SEQ ID NO:18) (for Mefp-2; at 100 pmol/$\mu$L), 40 $\mu$L sterile water and 1.0 $\mu$L Accuzyme DNA Polymerase were added to a thin-walled 0.5 mL PCR tube. Amplification was performed on a PerkinElmer 9700 thermocycler (PerkinElmer, Inc.; Boston, Mass.) under the following conditions: 95° C.-3 minutes; 30 cycles of: 95° C.-30 seconds, 50° C.-1:00 minute, 72° C.-2:00 minutes; 72° C.-10:00 minutes; final hold at 4° C. The PCR reaction was analyzed on a 1% agarose gel.

Following first strand cDNA synthesis, PCR was carried out as described for clone #7: 1 $\mu$L cDNA, 5 $\mu$L 10× Buffer for Taq PCR buffer (Promega; Madison, Wis.), 1 $\mu$L dNTPs (at 10 mM each), 2 $\mu$L primer set 514 (SEQ ID NO: 17)/515(SEQ ID NO:18) (for Mefp-2; at 100 pmol/$\mu$L), 37.5 $\mu$L sterile water and 0.5 $\mu$L Taq DNA Polymerase were added to a thin-walled 0.5 mL PCR tube. Amplification was performed on a Perkin-Elmer 9700 thermocycler as described above for clone #2. The PCR reaction was analyzed on a 1% agarose gel.

Cloning was performed per the pYES2.1 TOPO TA Cloning Kit (Invitrogen; Carlsbad, Calif.). Transformants were picked and screened by restriction enzyme digestion (SacI and NotI double restriction digest, per New England BioLabs; Beverly, Mass.) and DNA sequencing. Clone designations #2 and #7 (SEQ ID NOs:1 and 3, respectively) were determined to be complete cDNA clones for Mefp-2.

DNA sequencing of all potential Mefp-2 clones was performed with a LiCor 4000L DNA Sequencer (LiCor Inc.; Lincoln, Nebr.) and with an ABI 3700 DNA Sequencer using BigDye v2.0 and v3.0 chemistries (Applied Biosystems; Foster City, Calif.). Oligonucleotide sequencing primers were obtained from Invitrogen cloning kits, LiCor, Operon Technologies, Inc. (Alameda, Calif.), and MWG Biotech (UK). Primers used with the LiCor sequencer were IRD 800 dye-labeled. Primers used with the Applied Biosystems sequencer were un-labeled. See Table 2 for details of DNA sequencing primers used.

Screening of the cDNA libraries was performed following 96-well plasmid preparation methods from various vendors (e.g. Qiagen (Alameda, Calif.) and Promega (Madison, Wis.)).

Sequencing primers designed for vector targets were designed based upon vector sequences provided by Invitrogen. Primers designed by the inventors for targeting DNA sequence of Mefp-2 were based upon clone #2, #7 and QTB10 consensus sequences.

Sequencing primers for vector targets were obtained from Invitrogen. Primers designed by inventors (labeled HS/FFR) for targeting the DNA sequence of Mefp-2 were based upon clone #2, #7 and QTB10 consensus sequence (SEQ ID NO: 1, 3, and 5).

TABLE 2

Sequencing Primers

| Primer | F/R | Target: Vector or DNA Sequence | DNA Sequence: 5' to 3' | nt |
|---|---|---|---|---|
| T7 (Standard) Invitrogen Corporation | F | pYES2 and pYES2.1/V5-His-TOPO | TAATACGACTCACTATAGGG (SEQ ID NO: 7) | 20 |
| V5C-term Reverse Invitrogen Corporation | R | pYES2.1/V5-His-TOPO | ACCGAGGAGAGGGTTAGGGAT (SEQ ID NO: 8) | 21 |
| 506 by HS/FFR | R | pYES2 | TTTCGGTTAGAGCGGATG (SEQ ID NO: 9) | 18 |
| 507 by HS/FFR | R | pYES2 | AGGGCGTGAATGTAAGCGTG (SEQ ID NO: 10) | 20 |
| 508 | F | Mefp-2 internal | TTTGGTCCAGAATGCGAG | 18 |

TABLE 2-continued

Sequencing Primers

| Primer | F/R | Target: Vector or DNA Sequence | DNA Sequence: 5' to 3' | nt |
|---|---|---|---|---|
| by HS/FFR | | | (SEQ ID NO: 11) | |
| Sq1 | F | Mefp-2 internal | CTTTGGCAGACTTTGCG | 17 |
| by HS/FFR | | | (SEQ ID NO: 12) | |
| Sq2 | F | Mefp-2 internal | ACGGAAAGTGCTCACCC | 17 |
| by HS/FFR | | | (SEQ ID NO: 13) | |
| Sq3 | F | Mefp-2 internal | AAGTGCTCACCCTTGGG | 17 |
| by HS/FFR | | | (SEQ ID NO: 14) | |
| FP-1 | F | pPDM-1 | CCCAATACGCAAACCGCCTCT | 21 |
| EpiCentre | | | (SEQ ID NO: 15) | |
| RP-1 | R | pPDM-1 | TTAGAAAAATAAACAAATAGGGGTT | 25 |
| EpiCentre | | | (SEQ ID NO: 16) | |

It should be noted that Epicentre FP-1 (SEQ ID NO: 15) and RP-1 (SEQ ID NO: 16) were used for Mefp-1 and not used for Mefp-2.

Expression of Mefp-2 Protein

Expression of recombinant Mefp-2 protein from clone #2, #7 and QTB10 (SEQ ID NO: 1, 3, and 5) is performed by following the protocol set forth by Invitrogen. Expression is performed with the pYES2 system in the yeast strain *Saccharomyces cerevisiae*. A 30-liter fermentor (Bio Flo 4500-New Brunswick Scientific; Edison, N.J.) is used to scale-up from the Invitrogen protocol.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. Accordingly, the invention is limited only by the following claims and equivalents thereto.

All publications and patent documents cited in this application are incorporated by reference in their entirety for all purposes to the same extent as if each individual publication or patent document were so individually denoted.

We claim:

1. An isolated nucleic acid sequence encoding an adhesive protein derived from a mollusk, comprising a nucleotide sequence encoding a polypeptide having 90% identity to SEQ ID NO:2.

2. The isolated nucleic acid sequence of claim 1, wherein the nucleotide sequence comprises the nucleotide sequence of SEQ ID NO:1, or a degenerate variant of SEQ ID NO:1.

3. The isolated nucleic acid sequence of claim 1, wherein the nucleotide sequence consists of SEQ ID NO:1.

4. The isolated nucleic acid sequence of claim 1, wherein the nucleotide sequence comprises at least 500 continuous nucleotides of SEQ ID NO:1.

5. The isolated nucleic acid sequence of claim 1, wherein the nucleotide sequence has at least 98% identity to SEQ ID NO:1.

6. The isolated nucleic acid sequence of claim 1, wherein the nucleotide sequence encodes a polypeptide having the sequence of SEQ ID NO:2 with a conservative amino acid substitution.

7. An expression vector comprising the isolated nucleotide sequence of claim 1, operably linked to an expression control sequence.

8. The isolated nucleic acid sequence of claim 1, wherein the nucleotide sequence encodes the polypeptide consisting of SEQ ID NO:2.

9. An isolated nucleic acid sequence encoding an adhesive protein derived from a mollusk, comprising a nucleotide sequence encoding a polypeptide having 90% identity to SEQ ID NO:4.

10. The isolated nucleic acid sequence of claim 9, wherein the nucleotide sequence comprises the nucleotide sequence of SEQ ID NO:3, or a degenerate variant of SEQ ID NO:3.

11. The isolated nucleic acid sequence of claim 9, wherein the nucleotide sequence consists of SEQ ID NO:3.

12. The isolated nucleic acid sequence of claim 9, wherein the nucleotide sequence comprises at least 500 contiguous nucleotides of SEQ ID NO:3.

13. The isolated nucleic acid sequence of claim 9, wherein the nucleotide sequence has at least 98% identity to SEQ ID NO:3.

14. The isolated nucleic acid sequence of claim 9, wherein the nucleotide sequence encodes a polypeptide having the sequence of SEQ ID NO:4 with a conservative amino acid substitution.

15. The isolated nucleic acid sequence of claim 9, wherein the nucleotide sequence encodes the polypeptide consisting of SEQ ID NO:4.

16. An expression vector comprising the nucleotide sequence of claim 9, operably linked to an expression control sequence.

17. An isolated nucleic acid sequence encoding an adhesive protein derived from a mollusk, comprising a nucleotide sequence encoding a polypeptide having 90% identity to SEQ ID NO:6.

18. The isolated nucleic acid sequence of claim 17, wherein the nucleotide sequence comprises the nucleotide sequence of SEQ ID NO:5, or a degenerate variant of SEQ ID NO:5.

19. The isolated nucleic acid sequence of claim 17, wherein the nucleotide sequence consists of SEQ ID NO:5.

20. The isolated nucleic acid sequence of claim 17, wherein the nucleotide sequence comprises at least 500 contiguous nucleotides of SEQ ID NO:5.

21. The isolated nucleic acid sequence of claim 1, wherein the nucleotide sequence has at least 98% identity to SEQ ID NO:5.

22. The isolated nucleic acid sequence of claim 17, wherein the nucleotide sequence encodes a polypeptide having the sequence of SEQ ID NO:6 with a conservative amino acid substitution.

23. The isolated nucleic acid sequence of claim 17, wherein the nucleotide sequence encodes the polypeptide consisting of SEQ ID NO:6.

24. An expression vector comprising the nucleotide sequence of claim 17, operably linked to an expression control sequence.

* * * * *

SEQUENCE LISTING

```
<160> NUMBER OF SEQ ID NOS: 23

<210> SEQ ID NO 1
<211> LENGTH: 1527
<212> TYPE: DNA
<213> ORGANISM: Mytilus edulis

<400> SEQUENCE: 1

atgttgtttt ctttctttct tttgcttact tgtacccagc tttgcctagg aacgtcacca     60

cgtccatatg atgatgatga ggatgactac acaccaccag tatacaagcc ttcaccatcg    120

agatatcgac cagtaaaccc ctgtttaaag aagccatgta aatacaatgg agtatgtaaa    180

cccagtggtg gctcctacaa atgtgtctgc aaaggaggat actatggata caattgcaac    240

ctaaaaaacg catgtaaacc aaaccaatgt aaaaataaaa gtagatgtat acctgttgga    300

aaaacattta aatgtgaatg tagaaatgga aactttggca gactttgcga aagaaatgta    360

tgtagcccta atccttgtaa gaacaaagga aagtgcgccc ccttgggaaa gacaggatat    420

aaatgtacat gtagtggagg atacactggt ccccgatgtg aagttcatgc ttgcaaacca    480

aatccatgta aaaacaatgg aagatgttat cccgatggca aaacaggata taaatgtaaa    540

tgtgtcggag gatactcagg acctacatgt caagaaaacg cctgtaaacc aaacccctgt    600

agaaatggtg gaaaatgttc agcagacaaa tttggagact acacatgcga ttgtcgtcca    660

ggatattttg gtccacaatg cgagaagtat gtgtgtgccc ctaatccatg taaaaacagc    720
```

-continued

```
gggatatgtt catctgatgg cagcggtggt tacagatgta aatgtaaagg aggatactct    780

ggtcctacat gtaaagttaa tgtctgtaaa cccaacccac gcaagaacag tggcagatgt    840

gtcaacaaag gcagtagtta caactgtatc tgtaaaggag gttattctgg acctacatgt    900

ggagttaatg cctgtaaacc caatccatgc aagaacagtg gcagatgtgt caacaaaggc    960

agtagttaca actgtatctg taaaggaggt tattctggac ctaaatgtgg agaacatgtt   1020

tgtaaaccta atccatgcca aaatagaggt cgttgtgttc ccgaaggacg tgatggttac   1080

agatgtaaat gcgtaggtgg atattccggt cctacttgtg atgaaaatgt atgtaaaccc   1140

aatccttgtc aaaacaaagg cagatgctac cctgacaaca gtgatgatgg gtttaaatgt   1200

agatgtttag gaggatacaa aggtcctaca tgtgaagata aaccaaaccc atgtaacaca   1260

aaaccttgca aaaacggagg aaaatgtaat tataatggaa aacttatac ctgtaaatgt   1320

gcttacggat atcgtggaag acattgtact gctaaagcat ataaaccaaa cccatgtgct   1380

tcaagacctt gcaaaaatag aggaaagtgt actgttaaag gtaccggata tgtgtgtaca   1440

tgtgcaaaag gatatagtgg cagatattgt gcccttaaat caccaccatc ctacaacgat   1500

gatgacgagt attaagttaa cctagac                                       1527
```

<210> SEQ ID NO 2
<211> LENGTH: 508
<212> TYPE: PRT
<213> ORGANISM: Mytilus edulis

<400> SEQUENCE: 2

```
Met Leu Phe Ser Phe Phe Leu Leu Leu Thr Cys Thr Gln Leu Cys Leu
1               5                   10                  15

Gly Thr Ser Pro Arg Pro Tyr Asp Asp Asp Glu Asp Asp Tyr Thr Pro
            20                  25                  30

Pro Val Tyr Lys Pro Ser Pro Ser Arg Tyr Arg Pro Val Asn Pro Cys
        35                  40                  45

Leu Lys Lys Pro Cys Lys Tyr Asn Gly Val Cys Lys Pro Ser Gly Gly
    50                  55                  60

Ser Tyr Lys Cys Val Cys Lys Gly Gly Tyr Tyr Gly Tyr Asn Cys Asn
65                  70                  75                  80

Leu Lys Asn Ala Cys Lys Pro Asn Gln Cys Lys Asn Lys Ser Arg Cys
                85                  90                  95

Ile Pro Val Gly Lys Thr Phe Lys Cys Glu Cys Arg Asn Gly Asn Phe
            100                 105                 110

Gly Arg Leu Cys Glu Arg Asn Val Cys Ser Pro Asn Pro Cys Lys Asn
        115                 120                 125

Lys Gly Lys Cys Ala Pro Leu Gly Lys Thr Gly Tyr Lys Cys Thr Cys
    130                 135                 140

Ser Gly Gly Tyr Thr Gly Pro Arg Cys Glu Val His Ala Cys Lys Pro
145                 150                 155                 160

Asn Pro Cys Lys Asn Asn Gly Arg Cys Tyr Pro Asp Gly Lys Thr Gly
                165                 170                 175

Tyr Lys Cys Lys Cys Val Gly Gly Tyr Ser Gly Pro Thr Cys Gln Glu
            180                 185                 190

Asn Ala Cys Lys Pro Asn Pro Cys Arg Asn Gly Gly Lys Cys Ser Ala
        195                 200                 205

Asp Lys Phe Gly Asp Tyr Thr Cys Asp Cys Arg Pro Gly Tyr Phe Gly
    210                 215                 220

Pro Gln Cys Glu Lys Tyr Val Cys Ala Pro Asn Pro Cys Lys Asn Ser
```

-continued

```
225                 230                 235                 240

Gly Ile Cys Ser Ser Asp Gly Ser Gly Gly Tyr Arg Cys Lys Cys Lys
                245                 250                 255

Gly Gly Tyr Ser Gly Pro Thr Cys Lys Val Asn Val Cys Lys Pro Asn
            260                 265                 270

Pro Arg Lys Asn Ser Gly Arg Cys Val Asn Lys Gly Ser Ser Tyr Asn
        275                 280                 285

Cys Ile Cys Lys Gly Gly Tyr Ser Gly Pro Thr Cys Gly Val Asn Ala
    290                 295                 300

Cys Lys Pro Asn Pro Cys Lys Asn Ser Gly Arg Cys Val Asn Lys Gly
305                 310                 315                 320

Ser Ser Tyr Asn Cys Ile Cys Lys Gly Gly Tyr Ser Gly Pro Lys Cys
                325                 330                 335

Gly Glu His Val Cys Lys Pro Asn Pro Cys Gln Asn Arg Gly Arg Cys
            340                 345                 350

Val Pro Glu Gly Arg Asp Gly Tyr Arg Cys Lys Cys Val Gly Gly Tyr
        355                 360                 365

Ser Gly Pro Thr Cys Asp Glu Asn Val Cys Lys Pro Asn Pro Cys Gln
    370                 375                 380

Asn Lys Gly Arg Cys Tyr Pro Asp Asn Ser Asp Asp Gly Phe Lys Cys
385                 390                 395                 400

Arg Cys Leu Gly Gly Tyr Lys Gly Pro Thr Cys Glu Asp Lys Pro Asn
                405                 410                 415

Pro Cys Asn Thr Lys Pro Cys Lys Asn Gly Gly Lys Cys Asn Tyr Asn
            420                 425                 430

Gly Lys Thr Tyr Thr Cys Lys Cys Ala Tyr Gly Tyr Arg Gly Arg His
        435                 440                 445

Cys Thr Ala Lys Ala Tyr Lys Pro Asn Pro Cys Ala Ser Arg Pro Cys
    450                 455                 460

Lys Asn Arg Gly Lys Cys Thr Val Lys Gly Thr Gly Tyr Val Cys Thr
465                 470                 475                 480

Cys Ala Lys Gly Tyr Ser Gly Arg Tyr Cys Ala Leu Lys Ser Pro Pro
                485                 490                 495

Ser Tyr Asn Asp Asp Asp Glu Tyr Val Asn Leu Asp
            500                 505


<210> SEQ ID NO 3
<211> LENGTH: 1413
<212> TYPE: DNA
<213> ORGANISM: Mytilus edulis

<400> SEQUENCE: 3

atgttgtttt ctttcttact tttgcttact tgtacccagc tttgcctagg aacgtcacca      60

cgtccatatg atgatgatga ggatgactac tcaccaccag tatacaagcc ttcaccatcg     120

aaatatcgac cagtaaaccc ctgtttaaag aagccatgta aatacaatgg agtatgtaaa     180

cccaatggtg gctcctataa atgtacctgc aaaggaggat actatggata caactgcaac     240

ctaaaaaacg catgtaaacc aaaccaatgt aaaaataaag gtagatgttt acctgttgga     300

aaaacattta aatgtgtatg tagaaatgga aactttggca gactttgcga aagaaatgta     360

tgtagcccta atccttgtaa gaacaaagga aagtgcgccc cctggggaaa gacaggatat     420

aaatgtagat gtagtggagg atacactggt ccccgatgtg aagtacatgc ttgcaaacca     480

aacccatgta aaaacaaggg aagttgtaag cccgatggca aaacaggata taaatgtaca     540
```

-continued

```
tgtgtcggag gatactcagg acctacatgt caagaaaacg cttgtaaacc aaacccctgt    600

agcaatggag ggaaatgctc agctgacaaa tttggagact actcatgcga atgtcaaaaa    660

ggatattatg gtccagaatg cgagaaatat gtctgtgccc ctaatccatg taaaaacggc    720

gggaaatgtt cttctgatgg tagcggtggt tacaaatgtc aatgtaccgg aggatactca    780

ggtctaacat gtaatgttaa tgtctgtaaa cccaatccat gcaagaacag tggcagatgt    840

gtcaacaaag gcagtagtta caaatgtatc tgtaaaggag gatattctgg acctacatgt    900

ggagaacatg tatgtaaacc taatccatgc cagaatagag gtcgttgtta tcccgaagga    960

cgggatggtt acagatgtaa atgcgtaggt ggatattccg gtcctacttg tgatgaagat   1020

gtatgtaaac ccaatccatg tcagaacaaa ggcagatgtt accctgacaa gagtgatgat   1080

gggtttaaat gtaaatgtct aggaggatac acaggtccta catgtgaaga taaaccaaac   1140

ccatgtaaca caaaaccttg caaaaacgga ggaaaatgta gttataatgg gaaaacttat   1200

acctgtaaat gtgcttatgg ataccgtgga agacattgta ctgctaaagc atataaccca   1260

tgtgcttcaa gaccttgcaa aaatagagga aagtgtactg ttaaaggtac caaatatgtg   1320

tgtacatgtg caaaaggata tagtggcaga tattgtgccc ttaaatcacc accatcctac   1380

aacgatgatg acgagtatta agttaaccta gac                                1413
```

<210> SEQ ID NO 4
<211> LENGTH: 470
<212> TYPE: PRT
<213> ORGANISM: Mytilus edulis

<400> SEQUENCE: 4

```
Met Leu Phe Ser Phe Leu Leu Leu Leu Thr Cys Thr Gln Leu Cys Leu
1               5                   10                  15

Gly Thr Ser Pro Arg Pro Tyr Asp Asp Asp Glu Asp Asp Tyr Ser Pro
            20                  25                  30

Pro Val Tyr Lys Pro Ser Pro Ser Lys Tyr Arg Pro Val Asn Pro Cys
        35                  40                  45

Leu Lys Lys Pro Cys Lys Tyr Asn Gly Val Cys Lys Pro Asn Gly Gly
    50                  55                  60

Ser Tyr Lys Cys Thr Cys Lys Gly Gly Tyr Tyr Gly Tyr Asn Cys Asn
65                  70                  75                  80

Leu Lys Asn Ala Cys Lys Pro Asn Gln Cys Lys Asn Lys Gly Arg Cys
                85                  90                  95

Leu Pro Val Gly Lys Thr Phe Lys Cys Val Cys Arg Asn Gly Asn Phe
            100                 105                 110

Gly Arg Leu Cys Glu Arg Asn Val Cys Ser Pro Asn Pro Cys Lys Asn
        115                 120                 125

Lys Gly Lys Cys Ala Pro Trp Gly Lys Thr Gly Tyr Lys Cys Arg Cys
    130                 135                 140

Ser Gly Gly Tyr Thr Gly Pro Arg Cys Glu Val His Ala Cys Lys Pro
145                 150                 155                 160

Asn Pro Cys Lys Asn Lys Gly Ser Cys Lys Pro Asp Gly Lys Thr Gly
                165                 170                 175

Tyr Lys Cys Thr Cys Val Gly Gly Tyr Ser Gly Pro Thr Cys Gln Glu
            180                 185                 190

Asn Ala Cys Lys Pro Asn Pro Cys Ser Asn Gly Gly Lys Cys Ser Ala
        195                 200                 205

Asp Lys Phe Gly Asp Tyr Ser Cys Glu Cys Gln Lys Gly Tyr Tyr Gly
    210                 215                 220
```

-continued

```
Pro Glu Cys Glu Lys Tyr Val Cys Ala Pro Asn Pro Cys Lys Asn Gly
225                 230                 235                 240

Gly Lys Cys Ser Ser Asp Gly Ser Gly Gly Tyr Lys Cys Gln Cys Thr
                245                 250                 255

Gly Gly Tyr Ser Gly Leu Thr Cys Asn Val Asn Val Cys Lys Pro Asn
            260                 265                 270

Pro Cys Lys Asn Ser Gly Arg Cys Val Asn Lys Gly Ser Ser Tyr Lys
        275                 280                 285

Cys Ile Cys Lys Gly Gly Tyr Ser Gly Pro Thr Cys Gly Glu His Val
    290                 295                 300

Cys Lys Pro Asn Pro Cys Gln Asn Arg Gly Arg Cys Tyr Pro Glu Gly
305                 310                 315                 320

Arg Asp Gly Tyr Arg Cys Lys Cys Val Gly Gly Tyr Ser Gly Pro Thr
                325                 330                 335

Cys Asp Glu Asp Val Cys Lys Pro Asn Pro Cys Gln Asn Lys Gly Arg
            340                 345                 350

Cys Tyr Pro Asp Lys Ser Asp Asp Gly Phe Lys Cys Lys Cys Leu Gly
        355                 360                 365

Gly Tyr Thr Gly Pro Thr Cys Glu Asp Lys Pro Asn Pro Cys Asn Thr
    370                 375                 380

Lys Pro Cys Lys Asn Gly Gly Lys Cys Ser Tyr Asn Gly Lys Thr Tyr
385                 390                 395                 400

Thr Cys Lys Cys Ala Tyr Gly Tyr Arg Gly Arg His Cys Thr Ala Lys
                405                 410                 415

Ala Tyr Asn Pro Cys Ala Ser Arg Pro Cys Lys Asn Arg Gly Lys Cys
            420                 425                 430

Thr Val Lys Gly Thr Lys Tyr Val Cys Thr Cys Ala Lys Gly Tyr Ser
        435                 440                 445

Gly Arg Tyr Cys Ala Leu Lys Ser Pro Pro Ser Tyr Asn Asp Asp Asp
    450                 455                 460

Glu Tyr Val Asn Leu Asp
465                 470
```

<210> SEQ ID NO 5
<211> LENGTH: 1362
<212> TYPE: DNA
<213> ORGANISM: Mytilus edulis

<400> SEQUENCE: 5

```
atgttgtttt ctttctttct tttgcttact tgtacccagc tttgcctagg aacgtcacca      60

cgtcaatatg atgatgatga ggatgactac tcaccaccag tatacaagcc ttcaccatcg     120

aaatatcgac cagtaaaccc ctgtttaaag aagccatgca aatacaatgg agtatgtaaa     180

cccaatggtg gctcctataa atgtacctgc aaaggaggat actatggata caactgcaac     240

ctaaaaaacg catgtaaacc aaaccaatgt aaaaataaaa gtagatgtat acctgttgga     300

aaaacatata aatgtgtatg tagaaatgga aactatggca gactttgcga aaaaaatgta     360

tgtagcccta atccttgtaa gaacaaagga aagtgcgccc cctggggaaa gacaggatat     420

aaatgtagat gtagtggagg atacactggt ccccgatgtg aagtacatgc ttgcaaacca     480

aacccatgta aaaacaatgg aagttgtaag cccgatggca aaacaggata taaatgtaca     540

tgtgtcggag gatactcagg acctacatgt caagaaaacg cctgtaaacc aaacccctgt     600

agcaatggag ggaaatgctc agctgacaaa tttggagact actcatgcga atgtcaaaaa     660
```

-continued

```
agatattatg gtccagaatg cgagaaatat gtctgtgccc ctaatccatg taaaaatggc    720

gggaaatgtt cttctgatgg tagcggtggt tacaaatgtc aatgtaccgg aggatactca    780

ggtctaacat gtaatgttaa tgtctgtaaa cccaatccat gcaagaacag tggcagatgt    840

gtcaacaaag gcagtagtta caaatgtatc tgtaaaggag gatattctgg acctacatgt    900

ggagaaaatg tatgtaaacc caatccatgt cagaacaaag gcagatgtta ccctgaccag    960

agtgatgatg ggtttaaatg taaatgtcta ggaggataca caggtcctac atgtgaagat   1020

aaaccaaacc catgtaacac aaaaccttgc aaaaacggag gaaaatgtag ttataatggg   1080

aaaacttata cctgtaaatg tgcttatgga taccgtggaa gacattgtac tgctaaagca   1140

tataacccat gtgcttcaag accttgcaaa aatagaggaa agtgtactgt taaaggtacc   1200

aaatatgtgt gtacatgtgc aaaaggatat agtggcagat attgtgccct taaatcacca   1260

ccatcctaca acgatgatga cgagtattaa gttaacctag aaatttaaaa ttgtttttca   1320

ttattaaagg atatttgata ttcaaaaaaa aaaaaaaaaa aa                      1362


<210> SEQ ID NO 6
<211> LENGTH: 451
<212> TYPE: PRT
<213> ORGANISM: Mytilus edulis

<400> SEQUENCE: 6

Met Leu Phe Ser Phe Phe Leu Leu Leu Thr Cys Thr Gln Leu Cys Leu
1               5                   10                  15

Gly Thr Ser Pro Arg Gln Tyr Asp Asp Asp Glu Asp Asp Tyr Ser Pro
            20                  25                  30

Pro Val Tyr Lys Pro Ser Pro Ser Lys Tyr Arg Pro Val Asn Pro Cys
        35                  40                  45

Leu Lys Lys Pro Cys Lys Tyr Asn Gly Val Cys Lys Pro Asn Gly Gly
    50                  55                  60

Ser Tyr Lys Cys Thr Cys Lys Gly Gly Tyr Tyr Gly Tyr Asn Cys Asn
65                  70                  75                  80

Leu Lys Asn Ala Cys Lys Pro Asn Gln Cys Lys Asn Lys Ser Arg Cys
                85                  90                  95

Ile Pro Val Gly Lys Thr Tyr Lys Cys Val Cys Arg Asn Gly Asn Tyr
            100                 105                 110

Gly Arg Leu Cys Glu Lys Asn Val Cys Ser Pro Asn Pro Cys Lys Asn
        115                 120                 125

Lys Gly Lys Cys Ala Pro Trp Gly Lys Thr Gly Tyr Lys Cys Arg Cys
    130                 135                 140

Ser Gly Gly Tyr Thr Gly Pro Arg Cys Glu Val His Ala Cys Lys Pro
145                 150                 155                 160

Asn Pro Cys Lys Asn Asn Gly Ser Cys Lys Pro Asp Gly Lys Thr Gly
                165                 170                 175

Tyr Lys Cys Thr Cys Val Gly Gly Tyr Ser Gly Pro Thr Cys Gln Glu
            180                 185                 190

Asn Ala Cys Lys Pro Asn Pro Cys Ser Asn Gly Gly Lys Cys Ser Ala
        195                 200                 205

Asp Lys Phe Gly Asp Tyr Ser Cys Glu Cys Gln Lys Arg Tyr Tyr Gly
    210                 215                 220

Pro Glu Cys Glu Lys Tyr Val Cys Ala Pro Asn Pro Cys Lys Asn Gly
225                 230                 235                 240

Gly Lys Cys Ser Ser Asp Gly Ser Gly Gly Tyr Lys Cys Gln Cys Thr
                245                 250                 255
```

-continued

```
Gly Gly Tyr Ser Gly Leu Thr Cys Asn Val Asn Val Cys Lys Pro Asn
            260                 265                 270

Pro Cys Lys Asn Ser Gly Arg Cys Val Asn Lys Gly Ser Ser Tyr Lys
        275                 280                 285

Cys Ile Cys Lys Gly Gly Tyr Ser Gly Pro Thr Cys Gly Glu Asn Val
    290                 295                 300

Cys Lys Pro Asn Pro Cys Gln Asn Lys Gly Arg Cys Tyr Pro Asp Gln
305                 310                 315                 320

Ser Asp Asp Gly Phe Lys Cys Lys Cys Leu Gly Gly Tyr Thr Gly Pro
                325                 330                 335

Thr Cys Glu Asp Lys Pro Asn Pro Cys Asn Thr Lys Pro Cys Lys Asn
            340                 345                 350

Gly Gly Lys Cys Ser Tyr Asn Gly Lys Thr Tyr Thr Cys Lys Cys Ala
        355                 360                 365

Tyr Gly Tyr Arg Gly Arg His Cys Thr Ala Lys Ala Tyr Asn Pro Cys
    370                 375                 380

Ala Ser Arg Pro Cys Lys Asn Arg Gly Lys Cys Thr Val Lys Gly Thr
385                 390                 395                 400

Lys Tyr Val Cys Thr Cys Ala Lys Gly Tyr Ser Gly Arg Tyr Cys Ala
                405                 410                 415

Leu Lys Ser Pro Pro Ser Tyr Asn Asp Asp Asp Glu Tyr Val Asn Leu
            420                 425                 430

Glu Ile Asn Cys Phe Ser Leu Leu Lys Asp Ile Tyr Ser Lys Lys Lys
        435                 440                 445

Lys Lys Lys
    450


<210> SEQ ID NO 7
<211> LENGTH: 20
<212> TYPE: DNA
<213> ORGANISM: Artificial
<220> FEATURE:
<223> OTHER INFORMATION: T7 Sequencing Primer

<400> SEQUENCE: 7

taatacgact cactataggg                                                 20


<210> SEQ ID NO 8
<211> LENGTH: 21
<212> TYPE: DNA
<213> ORGANISM: Artificial
<220> FEATURE:
<223> OTHER INFORMATION: V5C-term Reverse Sequencing Primer

<400> SEQUENCE: 8

accgaggaga gggttaggga t                                               21


<210> SEQ ID NO 9
<211> LENGTH: 18
<212> TYPE: DNA
<213> ORGANISM: Artificial
<220> FEATURE:
<223> OTHER INFORMATION: Sequencing Primer 506-(HS-PYes2)

<400> SEQUENCE: 9

tttcggttag agcggatg                                                   18


<210> SEQ ID NO 10
<211> LENGTH: 20
```

-continued

```
<212> TYPE: DNA
<213> ORGANISM: Artificial
<220> FEATURE:
<223> OTHER INFORMATION: Sequencing Primer 507 (HS-PYes-2)

<400> SEQUENCE: 10

agggcgtgaa tgtaagcgtg                                                  20


<210> SEQ ID NO 11
<211> LENGTH: 18
<212> TYPE: DNA
<213> ORGANISM: Artificial
<220> FEATURE:
<223> OTHER INFORMATION: Sequencing Primer 508 (HS-Mefp-2 internal)

<400> SEQUENCE: 11

tttggtccag aatgcgag                                                    18


<210> SEQ ID NO 12
<211> LENGTH: 17
<212> TYPE: DNA
<213> ORGANISM: Artificial
<220> FEATURE:
<223> OTHER INFORMATION: Sequencing Primer Sq1 (HS-Mefp-2 internal)

<400> SEQUENCE: 12

ctttggcaga ctttgcg                                                     17


<210> SEQ ID NO 13
<211> LENGTH: 17
<212> TYPE: DNA
<213> ORGANISM: Artificial
<220> FEATURE:
<223> OTHER INFORMATION: Sequencing Primer SQ-2 (HS-Mefp-2 interna)

<400> SEQUENCE: 13

acggaaagtg ctcaccc                                                     17


<210> SEQ ID NO 14
<211> LENGTH: 17
<212> TYPE: DNA
<213> ORGANISM: Artificial
<220> FEATURE:
<223> OTHER INFORMATION: Sequencing Primer SQ-3 (HS-Mefp-2 internal)

<400> SEQUENCE: 14

aagtgctcac ccttggg                                                     17


<210> SEQ ID NO 15
<211> LENGTH: 21
<212> TYPE: DNA
<213> ORGANISM: Artificial
<220> FEATURE:
<223> OTHER INFORMATION: Sequencing Primer FP-1 (Epicentre)

<400> SEQUENCE: 15

cccaatacgc aaaccgcctc t                                                21


<210> SEQ ID NO 16
<211> LENGTH: 25
<212> TYPE: DNA
<213> ORGANISM: Artificial
<220> FEATURE:
<223> OTHER INFORMATION: Sequencing Primer RP-1 (Epicentre)

<400> SEQUENCE: 16
```

-continued

```
ttagaaaaat aaacaaatag gggtt                                           25


<210> SEQ ID NO 17
<211> LENGTH: 31
<212> TYPE: DNA
<213> ORGANISM: Artificial
<220> FEATURE:
<223> OTHER INFORMATION: PCR Primer 514-Mefp-2

<400> SEQUENCE: 17

gcggccgcca cagaagcatc atgttgtttt c                                    31


<210> SEQ ID NO 18
<211> LENGTH: 30
<212> TYPE: DNA
<213> ORGANISM: Artificial
<220> FEATURE:
<223> OTHER INFORMATION: PCR Primer 515-Mefp-2

<400> SEQUENCE: 18

gagctcgtct aggttaactt aatactcgtc                                      30


<210> SEQ ID NO 19
<211> LENGTH: 1489
<212> TYPE: DNA
<213> ORGANISM: Mytilus galloprovincialis

<400> SEQUENCE: 19

gtcacagaag catcatgttg ttttctttct ttcttttgct tacttgtacc cagctttgcc      60

taggaactaa tcgacctgat tataatgatg atgaggagga tgactacaaa ccaccagtat     120

acaagccttc accatcgaaa tatcgaccag taaacccctg tttaaagaag ccatgtaaat     180

acaatggagt atgtaaaccc agaggtggct cctacaaatg tttctgcaaa ggaggatact     240

atggatacaa ttgcaaccta aaaaacgcat gtaaaccaaa ccaatgtaaa aataaaagta     300

gatgtgtacc tgttggaaaa acatttaaat gtgtatgtag aaatggaaac tttggcagac     360

tttgcgaaaa aaatgtatgt agcccgaatc cttgtaaaaa caacggaaag tgctcaccct     420

tgggaaagac aggatataaa tgtacatgta gtggaggata cactggtccc cgatgtgaag     480

tgcatgcttg caaaccaaat ccatgtaaaa acaaaggaag atgttttccc gatggtaaaa     540

cagggtataa atgtagatgt gtcgacggat actcaggacc tacatgtcag gaaaacgcct     600

gtaaaccaaa cccatgtagc aatggaggga catgctcagc tgacaaattt ggagactact     660

catgcgaatg tcgcccagga tattttggtc cagaatgcga gaggtatgtg tgtgccccta     720

atccatgtaa aaacggcggc atatgttcat ctgatggcag cggcggttac agatgtagat     780

gtaaaggagg atactctggt cctacatgta aagtaaatgt ctgtaaaccc actccatgca     840

agaacagtgg cagatgtgtc aacaaaggca gtagttacaa ctgtatctgt aaaggaggtt     900

attctgggcc tacatgtgga gaaaatgtat gtaaacccaa tccatgtcaa aacagaggca     960

gatgttaccc tgacaacagt gatgatgggt ttaaatgtag atgtgtagga ggttacaaag    1020

gtcctacatg tgaagataaa ccaaacccat gcaacacaaa accttgcaaa aatggaggaa    1080

aatgtaatta taatggaaaa atttatacct gtaaatgtgc atacggatgg cgtggacgac    1140

attgtactga taaagcttat aaaccaaacc cttgtgttgt ttcaaagcca tgcaaaaaca    1200

gaggaaagtg tatttggaat ggaaaagctt atagatgcaa atgcgcatat ggatacggcg    1260

gcaggcattg cactaaaaaa tcatataaaa aaaacccatg tgcttcacgt ccatgtaaaa    1320

atagaggaaa gtgtacagat aaaggaaacg gatatgtgtg taaatgtgcc agaggataca    1380
```

```
gtggcagata ttgttctcta aaatcaccac catcctacga cgatgacgag tattaagtta   1440

acctagacat ttaaaattgt ttttcattat taaaggatat ttgatattc               1489


<210> SEQ ID NO 20
<211> LENGTH: 4
<212> TYPE: PRT
<213> ORGANISM: Artificial
<220> FEATURE:
<223> OTHER INFORMATION: Amino Acid Sequence ofor 514 primer

<400> SEQUENCE: 20

Met Leu Phe Ser
1


<210> SEQ ID NO 21
<211> LENGTH: 4
<212> TYPE: PRT
<213> ORGANISM: Artificial
<220> FEATURE:
<223> OTHER INFORMATION: Amino Acid Sequence for Primer 515
<220> FEATURE:
<221> NAME/KEY: misc_feature
<222> LOCATION: (4)..(4)
<223> OTHER INFORMATION: Xaa can be any naturally occurring amino acid

<400> SEQUENCE: 21

Asp Glu Tyr Xaa
1


<210> SEQ ID NO 22
<211> LENGTH: 6
<212> TYPE: PRT
<213> ORGANISM: Mytilus edulis

<400> SEQUENCE: 22

Ala Lys Pro Thr Tyr Lys
1               5


<210> SEQ ID NO 23
<211> LENGTH: 10
<212> TYPE: PRT
<213> ORGANISM: Mytilus edulis
<220> FEATURE:
<221> NAME/KEY: MOD_RES
<222> LOCATION: (3)..(3)
<223> OTHER INFORMATION: where P in residue 3 is trans-4-hydroxy-L-
      proline
<220> FEATURE:
<221> NAME/KEY: MOD_RES
<222> LOCATION: (5)..(5)
<223> OTHER INFORMATION: where Y in residue 5 is 3, 4-dihydroxyphenyl-
      alanine
<220> FEATURE:
<221> NAME/KEY: MOD_RES
<222> LOCATION: (6)..(6)
<223> OTHER INFORMATION: where P in residue 6 is trans-2,3-cis-3,4-
      dihydroxyproline
<220> FEATURE:
<221> NAME/KEY: MOD_RES
<222> LOCATION: (7)..(7)
<223> OTHER INFORMATION: where P in residue 7 is trans-4-hydroxy-L-
      proline
<220> FEATURE:
<221> NAME/KEY: MOD_RES
<222> LOCATION: (9)..(9)
<223> OTHER INFORMATION: where Y in residue 9 is 3, 4-dihydroxyphenyl-
      alanine
```

-continued

<400> SEQUENCE: 23

```
Ala Lys Pro Ser Tyr Pro Pro Thr Tyr Lys
1               5                   10
```